(12) United States Patent
Eisermann

(10) Patent No.: US 6,423,067 B1
(45) Date of Patent: Jul. 23, 2002

(54) NONLINEAR LAG SCREW WITH CAPTIVE DRIVING DEVICE

(75) Inventor: Lukas G. Eisermann, Memphis, TN (US)

(73) Assignee: Theken Surgical LLC, Barberton, OH (US)

( * ) Notice: Subject to any disclaimer, the term of this patent is extended or adjusted under 35 U.S.C. 154(b) by 0 days.

(21) Appl. No.: 09/560,443

(22) Filed: Apr. 28, 2000

Related U.S. Application Data (60) Provisional application No. 60/131,483, filed on Apr. 29, 1999.

(51) Int. Cl.[7] ................................................ A61B 17/86
(52) U.S. Cl. ...................................................... 606/65
(58) Field of Search ............................... 606/65, 66, 67, 606/68, 72, 73, 75, 59; 411/383, 387.3, 393, 402, 403, 407, 424, 426

(56) References Cited

U.S. PATENT DOCUMENTS

| | | | | |
|---|---|---|---|---|
| 161,390 A | * | 3/1875 | Cummings | 411/407 |
| 324,768 A | * | 8/1885 | Hunt | 606/72 |
| 367,011 A | * | 7/1887 | Rogers | 411/426 |
| 438,754 A | | 10/1890 | Rogers | |
| 2,771,262 A | * | 11/1956 | Laystrom | 411/383 |
| 3,054,321 A | * | 9/1962 | Macchia | 411/403 |
| 3,921,364 A | * | 11/1975 | Briles | 411/424 |
| 4,463,753 A | * | 8/1984 | Gustilo | 606/73 |
| 4,688,561 A | * | 8/1987 | Reese | 606/72 |
| 4,796,612 A | * | 1/1989 | Reese | 606/72 |
| 4,915,559 A | | 4/1990 | Wheeler | |
| 4,959,064 A | * | 9/1990 | Engelhardy | 606/65 |
| 5,084,050 A | * | 1/1992 | Draenert | 606/73 |
| 5,176,680 A | * | 1/1993 | Vignaud et al. | 606/73 |
| 5,259,398 A | * | 11/1993 | Vrespa | 606/65 |
| 5,380,325 A | | 1/1995 | Lahile | |
| 5,532,224 A | | 7/1996 | Westermann | |
| 5,549,683 A | | 8/1996 | Bonutti | |
| 5,569,247 A | | 10/1996 | Morrison | |
| 5,605,457 A | * | 2/1997 | Bailey et al. | 606/73 |
| 5,630,817 A | | 5/1997 | Rokegem | |
| 5,653,710 A | | 8/1997 | Harle | |
| 5,658,288 A | | 8/1997 | Kim | |
| 5,743,914 A | | 4/1998 | Skiba | |
| 5,849,004 A | * | 12/1998 | Bramlet | 606/73 |
| 5,964,768 A | | 10/1999 | Huebner | |
| 6,030,162 A | | 2/2000 | Huebner | |
| 6,053,920 A | * | 4/2000 | Carlsson et al. | 606/75 |

FOREIGN PATENT DOCUMENTS

FR 1105392 11/1995

\* cited by examiner

*Primary Examiner*—Eduardo C. Robert
(74) *Attorney, Agent, or Firm*—Frost Brown Todd LLC; Robert H. Eichenberger (57) ABSTRACT

A fastener is provided for fixating two objects in a fixed spatial relationship, such as bone segments, so that resultant stress is maintained at a constant value along a shank portion of the fastener in order to minimize stress concentrations and optimize the strength to size relationship of the fastener, thereby reducing the likelihood of fastener failure. The fastener additionally comprises an improved head which temporarily engages a driving instrument to facilitate fixation. A driving instrument for deploying the fastener is also provided.

27 Claims, 8 Drawing Sheets

NONLINEAR LAG SCREW WITH CAPTIVE DRIVING DEVICE

CROSS REFERENCES TO RELATED APPLICATIONS

This patent application claims priority from U.S. Provisional Patent Application Serial No. 60/131,483, filed Apr. 29, 1999.

STATEMENT REGARDING FEDERALLY SPONSORED RESEARCH OR DEVELOPMENT

Not applicable.

BACKGROUND OF THE INVENTION

The present invention relates to a fastener for holding two objects in a fixed spatial relationship with respect to one another, and more particularly to a screw-type fastener, and associated driving device, for fixating two bone segments in a fixed relationship.

The use of screw fixation to hold bone segments has been established as common practice in the surgical management and treatment of bone fractures. When fastening two segments together, it is often desirable to use a lag screw, having threads engaged in a distal bone segment and a smooth shank engaged in a proximal bone segment. Rotably engaging the fastener develops tension in the fastener assembly by advancing the distal bone segment along the long axis of the fastener until contact is made with the proximal bone segment. As the fastener assembly is further tightened, compressive stress is developed at the mating interface of the two bone segments, which has been shown to assist the fracture healing process.

As is well known, any device implanted into the human body, however, causes some type of tissue reaction to the implanted foreign material. For this reason, it is desirable to use the smallest feasible fasteners for fixating bone segments. Also, in some instances, there are definite anatomic limits to the size of fastener which may be employed for a particular condition.

One area where the anatomic limit is particularly notable is in anterior odontoid fracture fixation. In this condition, the dens portion of the second cervical vertebra has fractured, resulting in a bone segment being loose within the ring formed by the first cervical vertebra. Normally, the dens acts as a pivot around which the first cervical vertebra rotates. However, this pivot function is lost when the dens is fractured from the body of the second cervical vertebra. In order to restore the ability of the first cervical vertebra to rotate, and to prevent injury to the spinal cord, the dens is surgically accessed by an anterior inferior approach. An angled hole is drilled through the third cervical vertebra starting from the anterior face of the vertebral body, and leading in a path stopping at the inferior endplate of the second cervical vertebra. A smaller screw hole is drilled and then tapped from the caudal endplate of the second cervical vertebra through the center of the fractured dens. A screw, preferably a lag screw, is inserted through the body of the second cervical vertebra and into the fractured dens using some form of driving device. Rotably engaging the screw draws the fractured bone segment to the cephalad surface of the second cervical vertebra.

Effectively, the screw acts as a mechanical support for the dens to restore its function of acting as a pivot for the first cervical vertebra. The screw also allows compressive force to be developed at the fracture faces of the dens and the body of the second cervical vertebra, assisting the fracture healing process.

Surgical experience shows that standard straight-shank screws of the maximal diameter anatomically allowed often are insufficient for the surgical management of odontoid fractures. Often, the implant itself will fracture during healing due to high bending stresses imparted by the first cervical vertebra on the dens, and thereby in turn on the implant. Failures usually occur in areas of high stress concentrations, such as are developed in straight-shank beams loaded in bending conditions. Surgical experience also shows that, during the treatment of bone fractures and other surgical procedures, implantable fasteners can slip from the driving devices and into the patient.

Accordingly, an improved fastener is required to surgically manage odontoid fracture, effectively fixate other structures, and to prevent the accidental entry into the human body.

BRIEF SUMMARY OF INVENTION

The bone fastener of the present invention addresses and overcomes problems found in the prior art. In one aspect of the invention, a fastener for fixating two bone segments is provided, wherein the fastener has a helical thread portion for engaging a distal bone segment, a shank portion for spanning a proximal bone segment, and a head portion for acting as a stop or brake against the proximal bone segment. Also, a means to drive the fastener into the bone segments is provided.

In another aspect of the present invention, the thread portion of the fastener may be any sort of helical screw thread. It may be right-handed, left-handed, a machine thread, a cancellous bone thread, a buttress thread, or any other thread as is known in the art. Though a threaded fastener is described in a preferred embodiment, it is contemplated that the threaded portion may be replaced or augmented by non-threaded fastener means, such as bone hooks or anchors, or expanding barbs, including means which may be developed through the use of shape memory alloys.

In yet another aspect of the present invention, the shank portion of the present invention has a circular cross-section with a diameter that varies along the length of the shaft in a manner such that the resultant stress developed due to load applied in the distal bone segment is always a constant value. Maintaining the resultant stress at a constant value minimizes the development of stress concentrations and optimizes the strength vs. size relationship of the implanted component.

In a further aspect of the present invention, the head portion of the bone fastener has a diameter larger than the largest diameter of the shank portion of the fastener, so that the head portion acts as a stop against the proximal bone segment. In one present embodiment, the head portion also has a broached hex cavity and a smaller diameter internally threaded hole to facilitate driving and removing the fastener with a unique driving instrument.

In a final aspect, a driving instrument has a ball-type hex driver at its tip for engaging the broached hex cavity located in the head portion of the screw fastener. The driving instrument is further cannulated and accommodates a draw rod for engaging the threaded hole of the head portion of the bone fastener. Rotably engaging the draw rod while the ball-type hex is seated into the broached hex develops tension in the draw rod and bone fastener assembly, thereby firmly drawing the bone fastener to the driving instrument. The bone fastener may be driven without fear of it dropping off of the instrument and into the patient. Once the threaded portion of the fastener is engaged with the first bone segment, the draw rod may be removed, thereby allowing the ball-hex driver to drive the fastener at an angle from its centerline.

DETAILED DESCRIPTION OF THE PREFERRED EMBODIMENT

For the purposes of understanding the principles of the invention, references will now be made to the embodiments illustrated in the drawings. For ease of understanding, and for uniformity in structural terminology, the description will be directed to a fastener used in a surgical context. It should be appreciated, however, that the present invention is also contemplated for use in connection with fixation with body structures other than odontoid fixation. Similarly, the present invention also finds use for fixation of structures not found in the human body.

Figure 1:
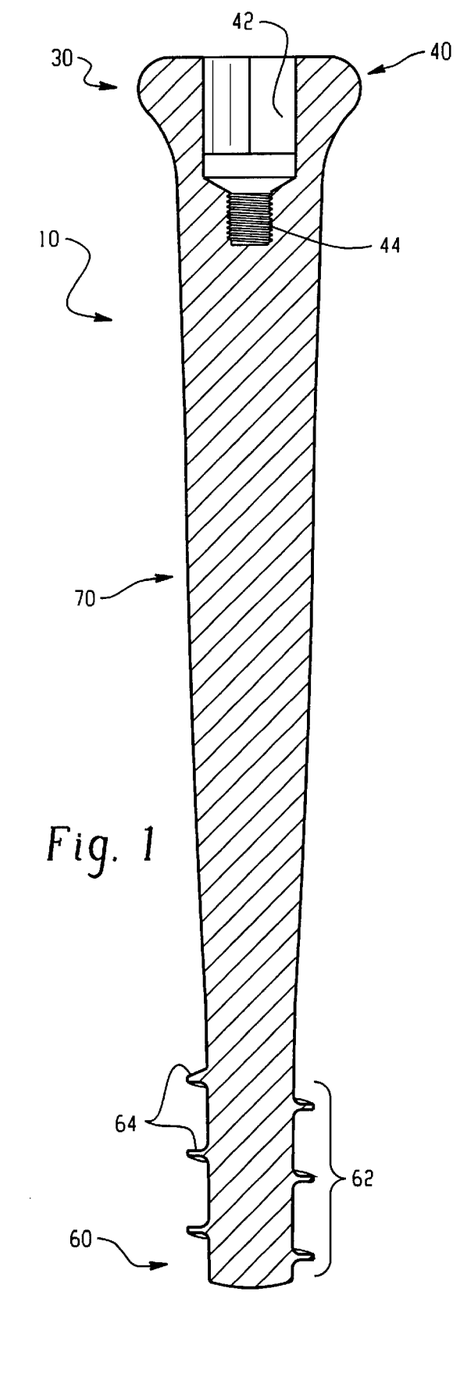
FIG. 1 is a longitudinal view of the bone fastener according to an embodiment of the present invention.

Referring now to the drawings, FIG. 1 shows a longitudinal view of a bone fastener 10 according to a preferred embodiment of the present invention.

As used herein, the term longitudinal axis shall take on its ordinary meaning in referring to an imaginary axis that runs through the length of the bone fastener 10. Likewise, as used herein, the term radial dimension shall take on its ordinary meaning in referring to a dimension that is measured orthogonally to the longitudinal axis in a given cross section of the bone fastener. In FIG. 1, the bone fastener 10 is a nonlinear taper lag screw. The bone fastener 10 comprises, generally, a proximal end 30, a distal end 60, and a variable diameter shank portion 70 therebetween.

The proximal end 30 typically further comprises a head 40. The head 40 further comprises an internal cavity 42 and a smaller internal threaded portion 44.

The distal end 60 typically further comprises an externally threaded portion 62 further comprising external threads 64. The external threads 64, as is known in the art, have associated therewith a minor root and a major root.

The shank portion 70 of the preferred embodiment has a circular cross-section that varies in diameter along the length of the shank portion 70 so that the resultant stress due to load applied in distal bone segment 66 is constant. Since the resultant stress remains constant, local stress concentrations decrease, thus greatly reducing the potential for failure of the bone fastener 10.

For the particular case of odontoid fixation described above, the shank portion 70 diameter is determined by the equation:

$$D(z)=[D(0)][(1-z/L)^{(1/3)}] \quad 0<z<L, D(z)>0. \quad \text{(Equation 1)}$$

where, z = the axial coordinate along the long axis of the screw;

L = the length of the bone fastener 10 in the current embodiment; and

D(z) is the diameter of the shank portion 70 in the current embodiment at a given coordinate, z.

It is contemplated that in some variations of the present invention, the variable L represents the length of only the variable diameter shank portion 70 of the bone fastener 10. In the preferred embodiment, z=0 at the head 40 of the bone fastener 10, and z=L at the most distal portion of the bone fastener 10. In the alternative variations of the present invention, z=0 at the head 40 of the bone fastener 10, and z=L at the most distal end of the shank portion 70.

From Equation 1:

$$\lim D(z)_{z \to L} = 0 \quad \text{(Equation 2)}$$

Equation 2 indicates that the actual varying diameter is carried out functionally only to the diameter of the minor root of the external threads 64.

It is further contemplated that in some variations of the present invention, a fastener with a non-circular cross section will replace the diameter variable with another appropriate dimension, such as the distance across flats in a hexagonal cross section, or the base or height in a rectangular cross section, the major or minor axes of an elliptical section, and so forth. One skilled in the art would readily appreciate that the form of Equation 1 would be appropriately modified for the non-circular cross section employed.

Figure 2:
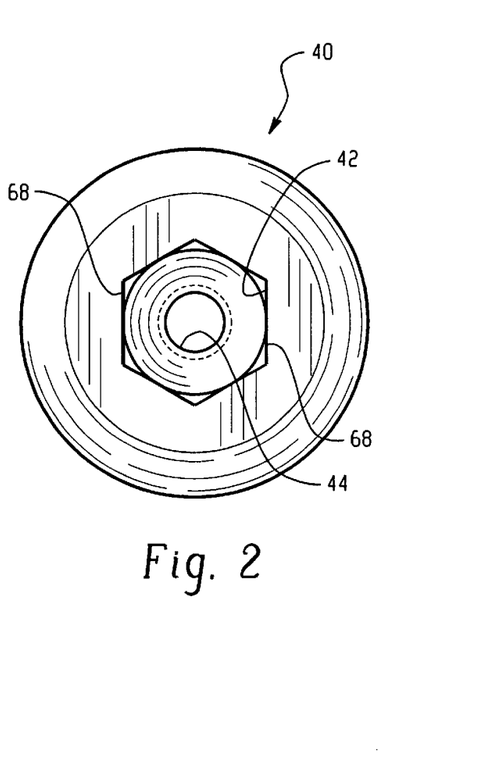
FIG. 2 is an axial view of the bone fastener according to an embodiment of the present invention.

FIG. 2 shows an axial view of the bone fastener 10 of the preferred embodiment. As illustrated, the head 40 contains an internal cavity 42 and an internal threaded portion 44. The internal cavity 42 defines, generally, a cavity or pocket taking the shape of an open polygonal cylinder. By this is meant that the open cylinder that is the cavity appears, in axial view, as a polygon. Referring to FIGS. 1 and 2, it can be seen that the internal cavity 42 further comprises at least two sidewalls 68. If the internal cavity 42 takes the shape of a slot, the internal cavity 42 will have two sidewalls 68. If the internal cavity 42 takes the shape of a cube or rectangular box, it will have four sidewalls 68. In the preferred embodiment depicted in FIGS. 1 and 2, the internal cavity 42 takes the shape of a hexagonal polygonal open cylinder, and therefore has six sidewalls 68. It is to be appreciated that the cavity further could take the shape of any regular open polygonal cylinder having at least three sides. Furthermore, the cavity could take the shape of any non-regular open polygonal cylinder, such as a star, or further any other irregular shape, and could also contain sidewalls 68 having differing dimensions.

FIGS. 1 and 2 also show that the head 40 of the preferred embodiment further has an internal threaded portion 44. The internal threaded portion 44 is used primarily to threadedly engage the bone fastener 10 with a driving instrument 100 in preparation of implantation, as will be described below. Once the bone fastener 10 and the driving instrument 100 are threadedly engaged, the bone fastener 10 will not accidentally fall into the patient.

Figure 3:
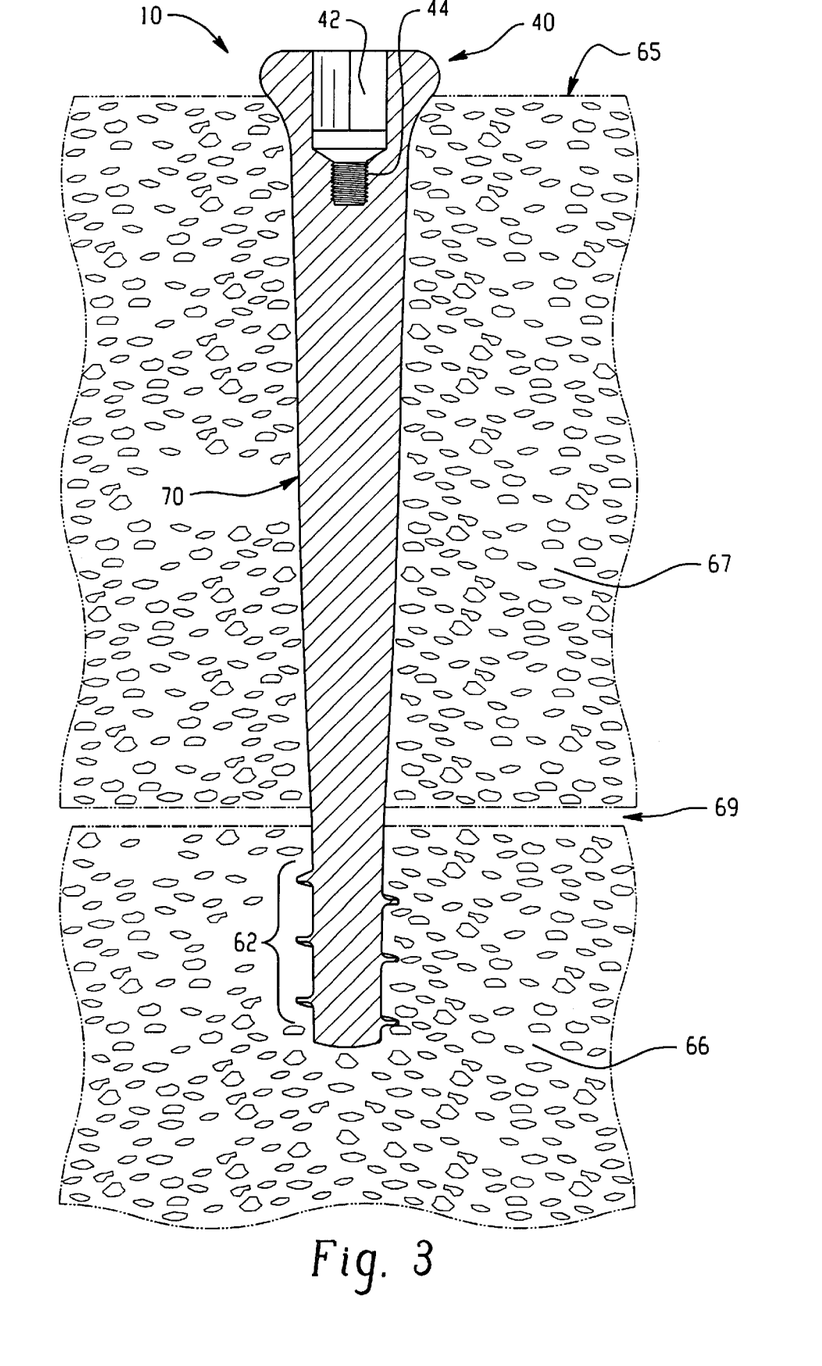
FIG. 3 is a representative view of the bone fastener according to an embodiment of the present invention engaging a proximal and distal bone segment.

FIG. 3 is a schematic representation of a longitudinal section of an embodiment of the bone fastener 10 of the present invention as implanted. The externally threaded portion 62 engages distal bone segment 66, while the shank portion 70 spans a proximal bone segment 67. Because the largest diameter of the head 40 of the bone fastener 10 is greater than the largest diameter of the shank portion 70, the head 40 seats against a surface 65 of the proximal bone segment 67. The bone fastener 10 can be tightened until the proximal bone segment 67 makes contact with the distal bone segment 66 at mating interface 69. After contact is made, the bone fastener 10 can be tightened further to create increased compressive stresses at mating interface 69 to facilitate the fracture healing process. The shape of the head 40 can be of many configurations and curvatures, including conical, tapered, non-linearly tapered, spherical, and any other configurations known in the art.

Figure 4A:
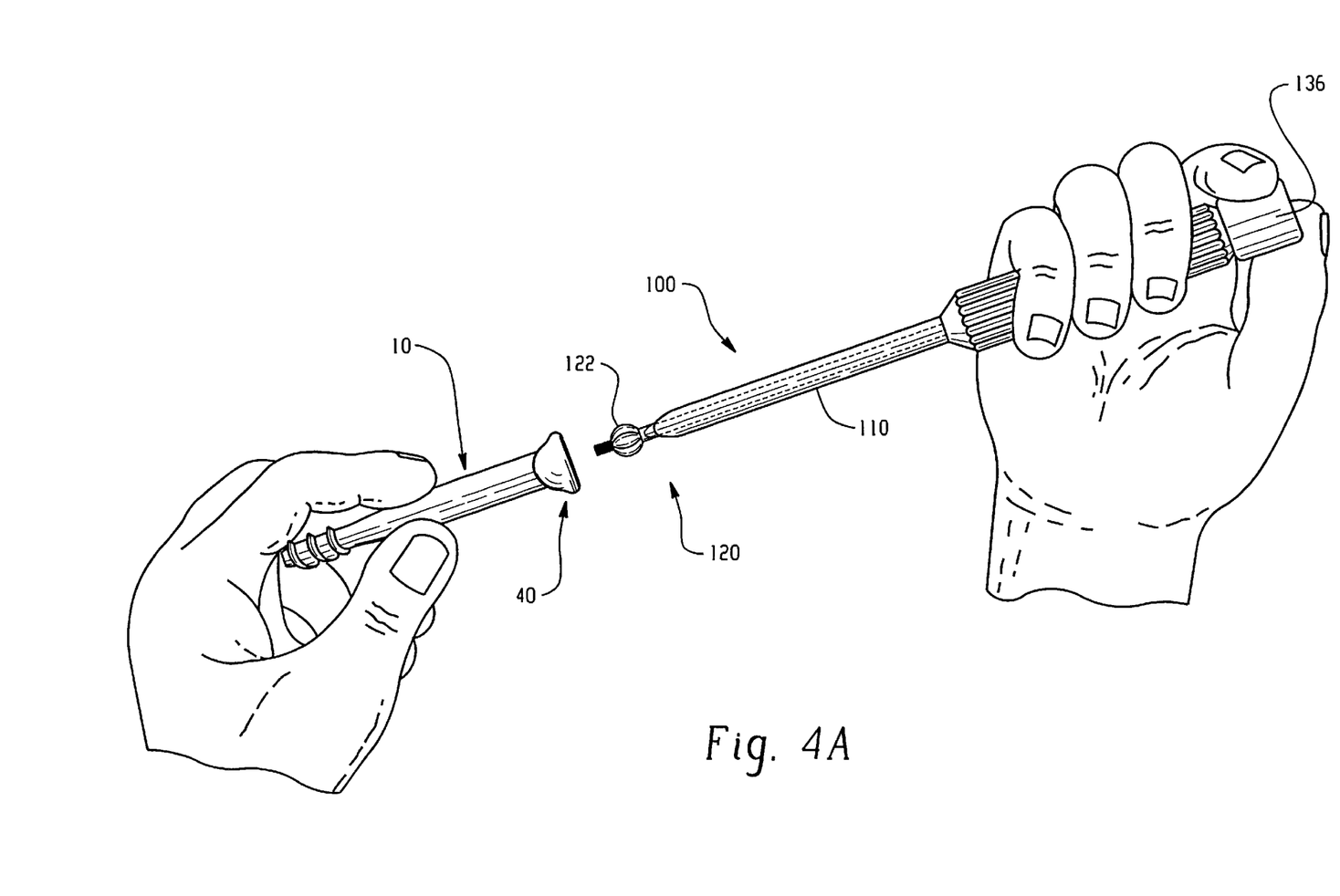
FIG. 4A is a perspective view of a bone fastener and driving mechanism according to an embodiment of the present invention prior to engagement of the bone fastener by the driving mechanism.

FIG. 4A is a perspective view of a driving instrument 100 for deploying the bone fastener 10. The driving instrument 100 has a cannulated shaft portion 110, a driving end 120 and a draw rod 130. The driving end 120 has a broached ball-type geometric portion 122 for engaging the internal geometric receiving portion of the head 40 of the bone fastener 10. The draw rod 130 typically has an external threaded portion 132, a shaft portion 134, and an activation portion 136. The draw rod 130 of the driving device 100 can additionally be fitted with a retention mechanism (not shown) to prevent the draw rod 130 from sliding out of the cannulated shaft portion 110 when the driving mechanism 100 is turned upside down. Such retention mechanisms can include, but are not limited to, ball detentes (comprising a ball and spring combination attached to either the cannulated shaft portion 110 or the draw rod 130, and a corresponding recess in the draw rod 130 or the cannulated shaft portion 110), or annular elastomeric rings attached to the draw rod 130 or the cannulated shaft portion 110. The external threaded portion 132 of the draw rod 130 is primarily used for engaging the internal threaded portion 44 of the bone fastener 10. The shaft portion 134 of the draw rod 130 has an external diameter that is smaller than the internal diameter of the cannulated shaft portion 110 of the driving instrument 100. This facilitates the easy removal of the draw rod 130 from the driving instrument 100. The activation portion 136 of the draw rod 130 allows the user to rotably engage and disengage the bone fastener 10 to and from the driving instrument 100. The broached ball-type geometric portion 122 at the driving end of the driving instrument 100 engages the internal cavity 42 of the bone fastener 10 for driving the bone fastener 10.

Figure 4B:
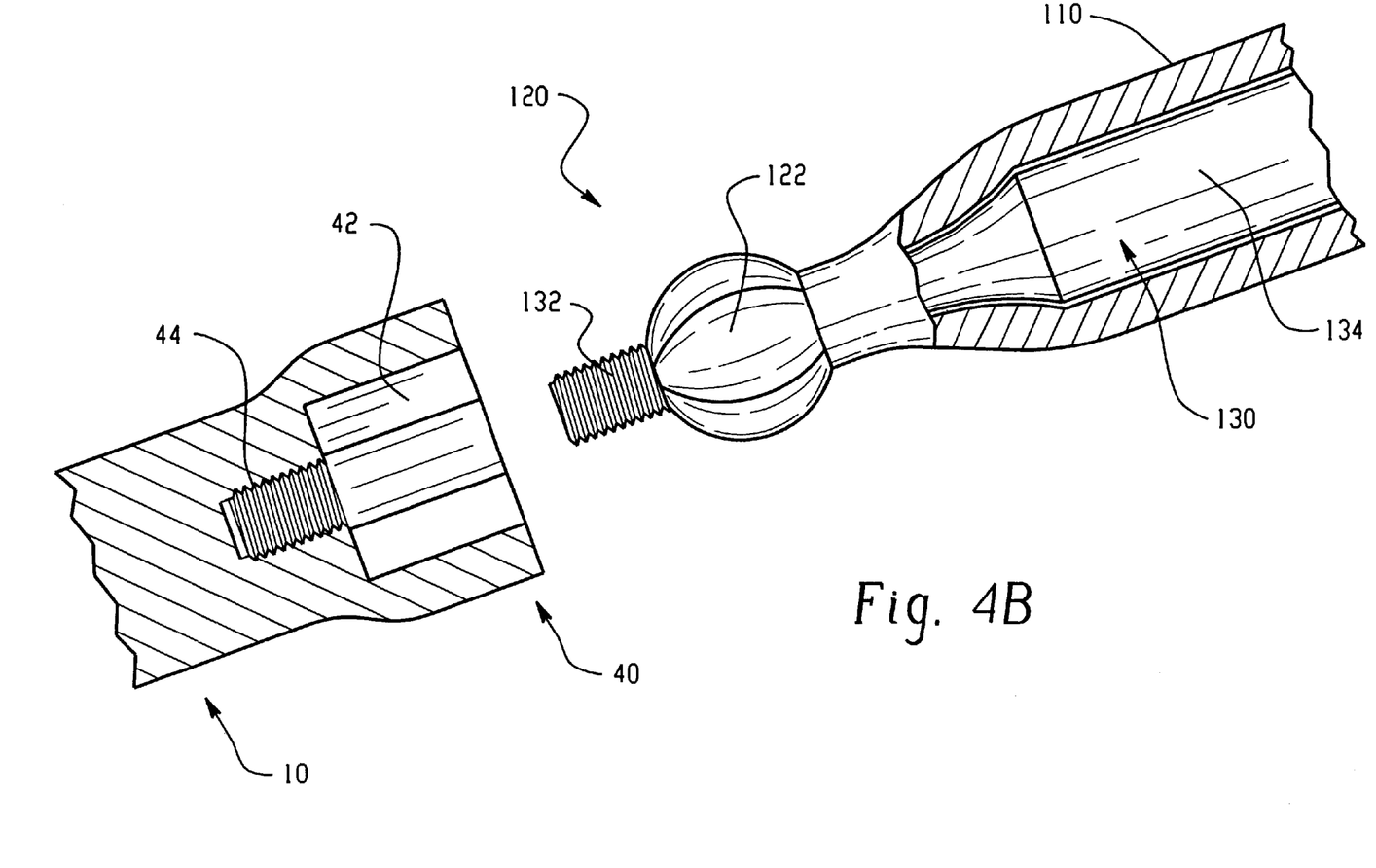
FIG. 4B is a detailed perspective view of FIG. 4A showing, in partial cross section, the head portion of a bone fastener according to an embodiment of the present invention, and the tip of the driving instrument just prior to engagement.

FIG. 4B is a detailed view of the driving end 120 of the driving instrument 100 and the head 40 of the bone fastener 10. As can be seen, the broached ball-type geometric portion 122 of the driving instrument 100 engages the internal cavity 42 of the head 40 of the bone fastener 10. In this manner it is readily apparent how other various geometries can be implemented for the broached ball-type geometric portion 122 of the driving instrument 100 and the internal cavity 42 of the head 40 of the bone fastener 10.

Figure 5:
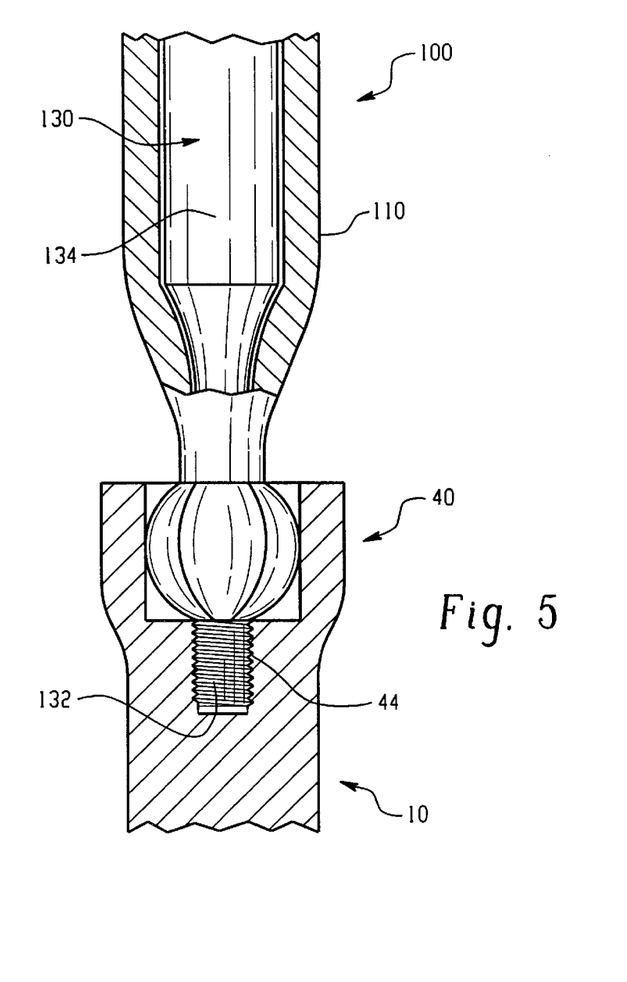
FIG. 5 is a view of a bone fastener and driving mechanism according to an embodiment of the present invention, showing the draw rod and ball-type hex driver and the bone fastener engaged for driving or removing.

FIG. 5 shows a cut-away view of the driving instrument 100 of FIGS. 4A and 4B engaged with the bone fastener 10. The external threaded portion 132 of the draw rod 130 is engaged with the internal threaded portion 44 of the bone fastener 10. The broached ball-type geometric portion 122 of the driving end 120 of the driving instrument 100 is engaged with the internal cavity 42 of the head 40 of the bone fastener 10.

Figure 6:
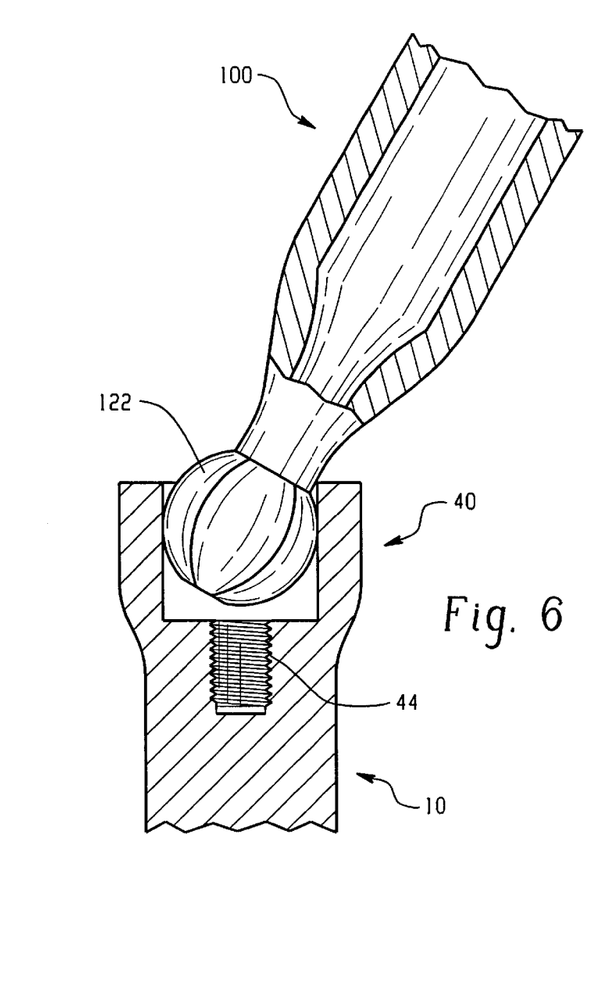
FIG. 6 is a view of a bone fastener and driving mechanism according to an embodiment of the present invention, showing the draw rod removed for angular driving.
Figure 7A:
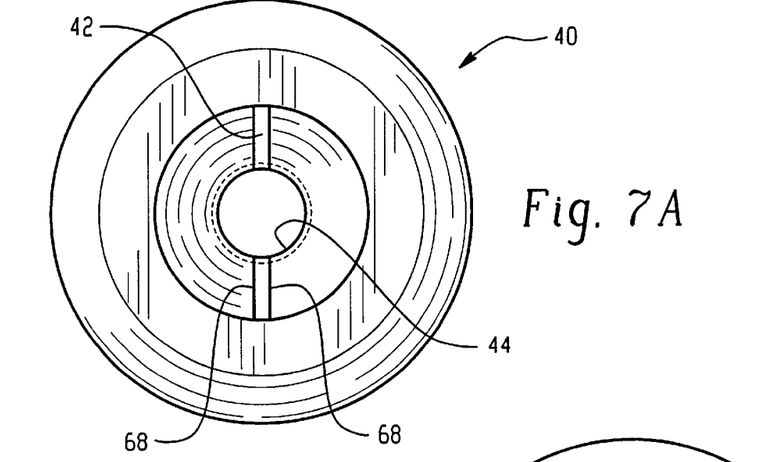
FIG. 7(a) depicts an embodiment of the invention wherein the internal cavity is slotted.
Figure 7B:
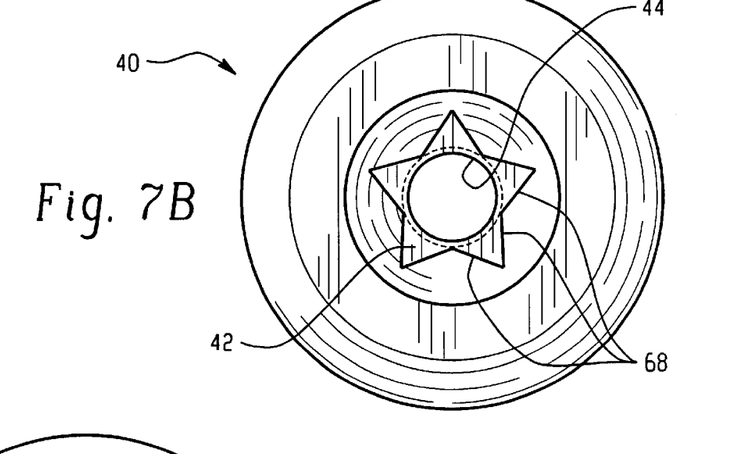
FIG. 7(b) depicts an embodiment of the invention wherein the internal cavity comprises a generalized open irregular polygonal cylinder having at least three sides.
Figure 7C:
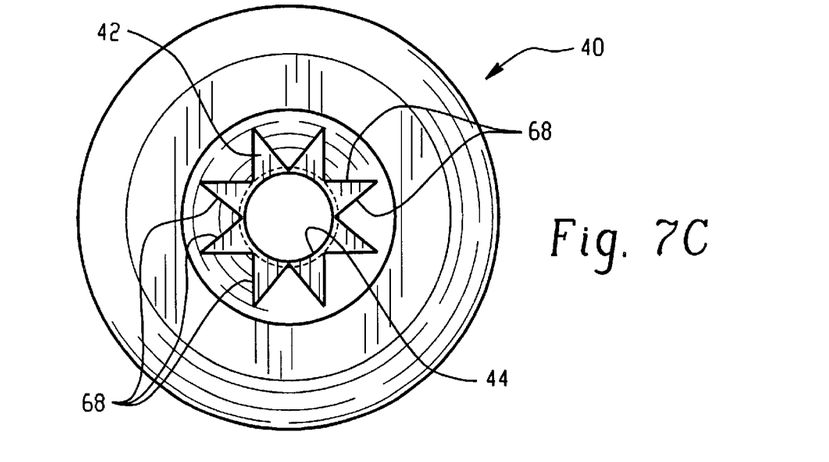
FIG. 7(c) depicts a further embodiment of the invention wherein the internal cavity comprises a generalized open irregular polygonal cylinder having at least three sides.
Figure 8:
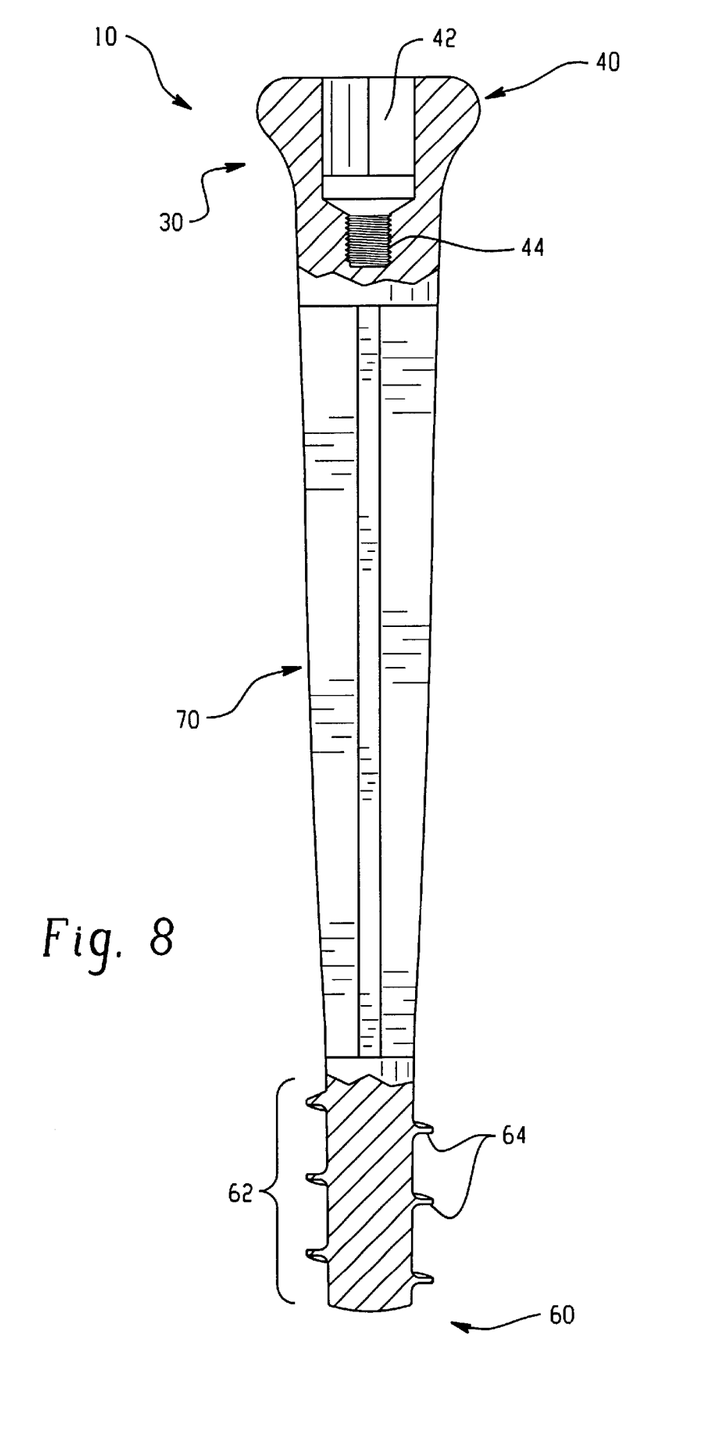
FIG. 8 depicts an embodiment of the invention wherein the shank portion further comprises a non-circular cross-section.
Figure 9A:
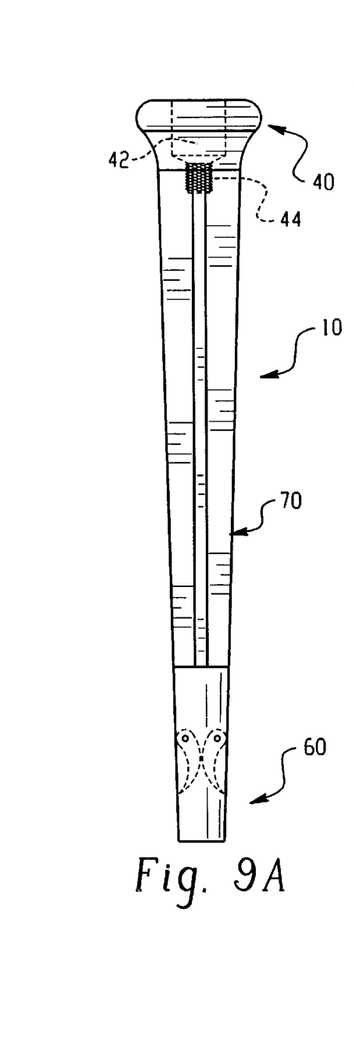
FIG. 9(a) depicts an embodiment of the invention wherein the fastener comprises a distal end having a non-threaded fastening mechanism in the form of an expanding barb attached thereto, wherein the expanding barb is depicted in the retracted position.
Figure 9B:
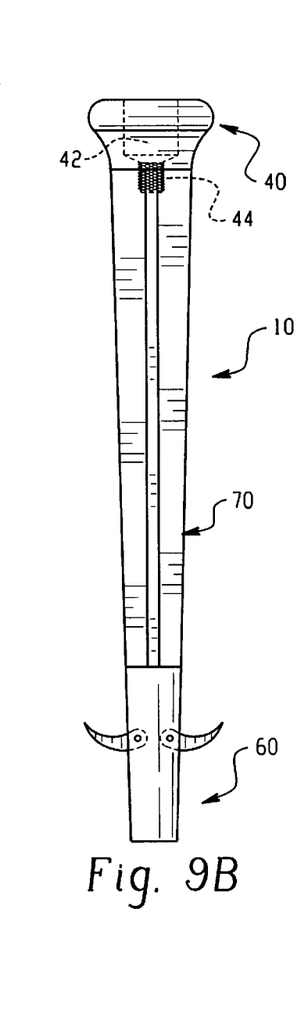
FIG. 9(b) depicts the fastener of FIG. 9(a) wherein the expanding barb is of a shape memory alloy and is depicted in the expanded position.
Figure 10A:
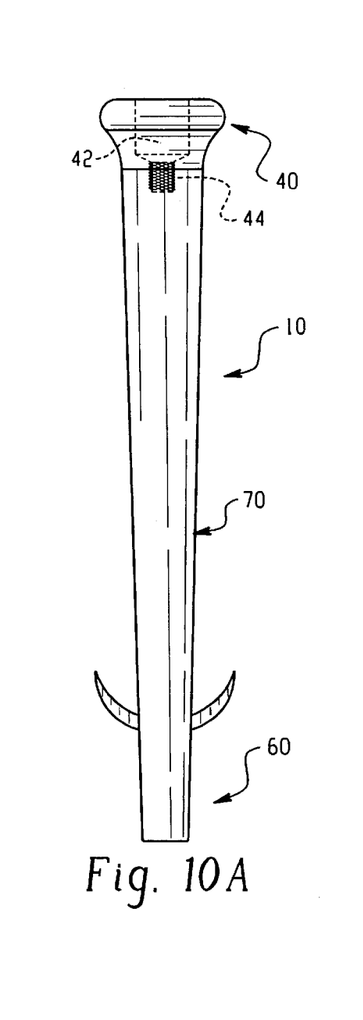
FIG. 10(a) depicts an embodiment of the invention wherein the fastener comprises a non-threaded fastening mechanism further comprising bone hooks.
Figure 10B:
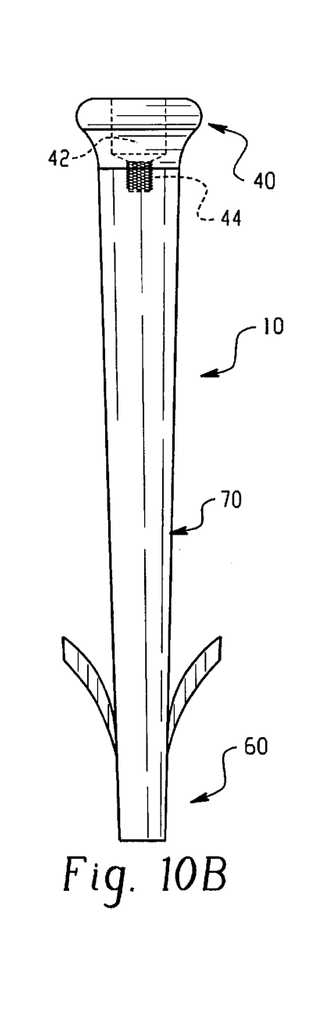
FIG. 10(b) depicts an embodiment of the invention wherein the fastener comprises a non-threaded fastening mechanism further comprising bone anchors.

FIG. 6 shows a cut-away view of the driving instrument 100 engaged with the bone fastener 10. The external threaded portion 132 of the draw rod 130 has been disengaged from the internal threaded portion 44 of the head 40 of the bone fastener 10, and the draw rod 130 itself has been removed from the driving instrument 100. In FIG. 6, the driving instrument 100 is shown disposed at an angle of inclination (angle of approach) with respect to the longitudinal axis of the bone fastener 10. In other words, the angle of inclination between the longitudinal axes of the driving instrument 100 and the bone fastener 10 is greater than zero. Despite the angle of inclination, however, it can be seen that the broached ball-type geometric portion 122 of the driving instrument 100 remains engaged with the internal cavity 42 of the head 40 of the bone fastener 10. This arrangement allows the bone fastener 10 to be driven into the bone structures at varying angles of inclination.

Referring to FIGS. 2, 4, 5, and 6, it is readily seen that the internal cavity 42 receives the driving end 120 of the driving instrument 100 in such a way that the driving instrument 100 can rotate the bone fastener 10 despite being inclined with respect to the longitudinal axis of the bone fastener 10. In the preferred embodiment, the internal cavity 42 is hexagonal. However, any geometric shape is possible for the internal cavity 42, including slotted, triangular, quadrangular, pentagonal, hexagonal, septagonal, octagonal, nonagonal, pentagonal, and n-tagonal, where n represents the number of sides of a regular polygon greater than 10. In addition, it is readily apparent to one skilled in the art that all other polygons, as well as any irregular shapes for the internal cavity 42 also come within the ambit of the present invention. The figures also show that the head 40 of the preferred embodiment further has an internal threaded portion 44. The internal threaded portion 44 is used primarily to threadedly engage the bone fastener 10 with the driving instrument 100 in preparation of implantation. Once the bone fastener 10 and the driving instrument 100 are threadedly engaged, the bone fastener 10 will not accidentally fall into the patient.

The bone fastener 10 can be made from virtually any material used in making devices and articles to be implanted in the human body. Often, the fastener will be made from a radiopaque material so that during imaging, the fastener can be readily observed. It is contemplated, however, that the fastener can also be made from radiolucent materials that are not readily observed during imaging. Likewise, some combination of radiopaque and radiolucent materials may be employed in order to create a marker that can be readily observed during imaging.

In the preferred embodiment of the present invention described above, the bone fastener 10 is described having a circular cross section. However, it would be readily apparent to one skilled in the art that the present invention is readily adaptable to fasteners having other polygonal cross sections, as well as irregular cross sections. Equation 1 need only be modified to apply to the particular non-circular cross section chosen.

Furthermore, in the preferred embodiment described above, the broached ball-type geometric portion 122 is hexagonal. However, any geometric shape may be possible for the broached geometric ball-type portion 122, including flat, triangular, quadrangular, pentagonal, hexagonal, septagonal, octagonal, nonagonal, pentagonal, and n-tagonal, where n represents the number of sides of a regular polygon greater than 10. In addition, it is readily apparent to one skilled in the art that irregular or other geometries for the broached ball-type geometric portion 122 also come within the ambit of the present invention.

Having described the structure of the bone fastener 10 of the preferred embodiment, the use of the bone fastener 10 can now described. Again, a surgical example is chosen for illustrative purposes, it being understood that non-surgical applications are equally applicable. Once the proper surgical preparations have been made, the user selects a bone fastener 10 of the appropriate size, material, and physical specifications. The draw rod 130 is inserted into the cannulated shaft portion 110 of the driving instrument 100 so as to engage the retaining mechanism (not shown), if any. Holding the driving instrument 100 and draw rod 130 in one hand, the user then inserts the broached ball-type geometric portion 122 of the driving end 120 of the driving instrument 100 into the internal cavity 42 of the head 40 of the bone fastener 10. Then, by rotating the activating portion 136 of the draw rod 130, the user engages the external threaded portion 132 of the draw rod 130 with the internal threaded portion 44 of the head 40. The user can continue rotably engaging the bone fastener 10 to the driving end 120 of the driving instrument 100 until the bone fastener 10 is securely engaged thereto.

Now, the bone fastener 10 is effectively an extension of the driving instrument 100. The user is able to drive the bone fastener 10 into the material (for example, into the proximal bone segment) without fear of the bone fastener 10 falling off of the driving instrument 100. In addition, once the bone fastener 10 has been started in the material, or at any point thereafter, the draw rod 130 can be removed from the driving instrument 100 by rotably disengaging the external threaded portion 132 from the internal threaded portion 44 of the head 40. The bone fastener 10 may be further driven into the material by rotably engaging the broached ball-type geometric portion 122 with the internal cavity 42 of the head 40. In addition, because of the broached ball-type geometric portion 122, the bone fastener 10 may be driven into the material at an angle of inclination from the longitudinal axis of the bone fastener 10. This facilitates driving the bone fastener 10 in locations or conditions requiring, for whatever reason, an angle of approach greater than zero.

What is claimed is:

1. A fastener comprising a proximal end, a distal end terminating in a tip, and a shank portion therebetween, said fastener having a longitudinal axis extending from said proximal end to said distal end and a radial axis orthogonal to said longitudinal axis said proximal end further comprising a head portion having in internal thread portion, said distal end further comprising, a threaded portion having a major root and a minor root commonly associated with threads, wherein said minor root defines a cross-section that varies non-linearly in radial dimension along said longitudinal axis from said tip to said shank portion, and wherein said shank portion likewise has a cross-section that varies non-linearly in radial dimension along said longitudinal axis of said fastener from said threaded portion to said proximal end.

2. The fastener according to claim 1 wherein said shank portion terminates at said threaded portion at a diameter equal to said minor root.

3. The fastener according to claim 1 wherein said head portion further comprises an internal cavity for receiving a driving instrument.

4. The fastener according to claim 3 wherein said internal cavity is slotted.

5. The fastener according to claim 3 wherein said internal cavity further comprises a generalized open regular polygonal cylinder having at least three sides.

6. The fastener according to claim 3 wherein said internal cavity further comprises a generalized open regular polygonal cylinder having at least six sides.

7. The fastener according to claim 3 wherein said internal cavity further comprises an open hexagonal cylinder.

8. The fastener according to claim 3 wherein said internal cavity further comprises an open irregular polygonal cylinder having at least three sides.

9. The fastener according to claim 1 wherein said shank portion further comprises a circular cross-section mathematically described such that constant stress exists therealong when load is applied to said threaded portion.

10. The fastener according to claim 1 wherein said shank portion further comprises a non-circular cross-section mathematically described such that constant stress exists therealong when load is applied to said threaded portion.

11. The fastener according to claim 1, wherein said cross section of said shank portion and of said minor root of said threaded portion is non-linearly proportional to a given axial distance along said longitudinal axis of said fastener measured from said proximal end.

12. The fastener according to claim 11, wherein said cross section of said shank portion and of said minor root of said threaded portion is determined by multiplying a diameter of said head by a cube root of a quantity: (one minus a quotient of (a) a given axial coordinate along said longitudinal axis of said fastener and (b) a total length of said fastener).

13. The fastener according to claim 11 wherein said cross section of said shank portion and of said minor root of said threaded portion varies non-linearly in radial dimension along said longitudinal axis of said fastener so that constant stress exists therealong when load is applied to said fastener.

14. The fastener according to claim 1, wherein said cross section of said shank portion and of said minor root of said threaded portion vary in dimension along said longitudinal axis of said fastener with a cube root of an axial coordinate along said longitudinal axis of said fastener.

15. The fastener according to claim 14 wherein said cross section of said shank portion and of said minor root of said threaded portion is determined by multiplying a diameter of said head by a cube root of a quantity: (one minus the quotient of (a) a given axial coordinate along said longitudinal axis of said fastener and (b) a total length of said fastener).

16. The fastener according to claim 14 wherein said cross section of said shank portion and of said minor root of said threaded portion varies non-linearly in radial dimension along said longitudinal axis of said fastener so that constant stress exists therealong when load is applied to said fastener.

17. A non-linearly tapered fastener having a longitudinal axis and a radial axis associated therewith comprising:

a) a proximal end, said proximal end further comprising a head having an external generally circular cross section of varying diameter, said head further having a maximum diameter and a minimum diameter, said head further comprising an internal cavity therein and an internal threaded portion, said internal cavity being open at said proximal end of said fastener and having a lower annular surface, and said internal threaded portion further comprising an entrance adjacent said lower annular surface of said internal cavity;

b) a distal end, said distal end further comprising an externally threaded portion terminating at a tip, said threaded portion having a major root and a minor root commonly associated with threads, wherein said minor root cross-sectional diameter at any given location varies non-linearly along said longitudinal axis; and c) a shank portion disposed between said proximal end and said distal end, said shank portion having a cross section varying nonlinearly in dimension along said longitudinal axis from said threaded portion to said head, wherein said dimension of said shank portion has a maximum value that is less than said maximum diameter of said head.

18. The fastener according to claim 17, wherein said cross section of said shank portion is circular.

19. The fastener according to claim 17, wherein said internal cavity is a generalized open hexagonal cylinder.

20. The fastener according to claim 17, wherein said entrance to said internal threaded cavity is disposed adjacent said bottom surface of said internal cavity.

21. A fastener comprising:

a) a proximal end, said proximal end further comprising a head having a maximum diameter and a minimum diameter, said head further comprising an internal cavity therein and an internal threaded portion, said internal cavity being open at said proximal end of said fastener and having a lower annular surface, and said internal threaded portion further comprising an entrance adjacent said lower annular surface of said internal cavity;

b) a distal end terminating at a tip, said distal end further comprising a non-threaded fastening mechanism attached thereto, wherein said distal end further comprises a cross-sectional dimension at any given location that varies non-linearly along said longitudinal axis; and c) a shank portion disposed between said proximal end and said distal end, wherein said distal end and said shank portion have a cross section nonlinearly varying in radial dimension along said longitudinal axis of said fastener, and wherein said shank portion has a maximum cross-sectional dimension that is less than said maximum diameter of said head.

22. The fastener according to claim 21, wherein said cross section of said shank portion is circular.

23. The fastener according to claim 21, wherein said internal cavity is a generalized open hexagonal cylinder.

24. The fastener according to claim 21, wherein said non-threaded fastening mechanism further comprises bone hooks.

25. The fastener according to claim 21, wherein said non-threaded fastening mechanism further comprises bone anchors.

26. The fastener according to claim 21, wherein said non-threaded fastening mechanism further comprises expanding barbs.

27. The fastener according to claim 21, wherein said non-threaded fastening mechanism further comprises shape memory alloys.

* * * * *